United States Patent [19]
Mills

[11] Patent Number: 5,409,018
[45] Date of Patent: Apr. 25, 1995

[54] SURGICAL DRAPE WITH RETRACTOR TUNNELS

[75] Inventor: Veronica A. Mills, Cincinnati, Ohio

[73] Assignee: Standard Textile Co., Inc., Cincinnati, Ohio

[21] Appl. No.: 120,090

[22] Filed: Sep. 13, 1993

[51] Int. Cl.⁶ .................................................. A61B 19/08
[52] U.S. Cl. .............................. 128/852; 128/853; 128/849
[58] Field of Search .............................. 128/849–856; 433/137, 136; 5/495, 497, 485, 482

[56] References Cited

U.S. PATENT DOCUMENTS

| | | | |
|---|---|---|---|
| 3,800,790 | 4/1974 | Collins . | |
| 3,823,709 | 7/1974 | McGuire | 128/850 |
| 3,910,268 | 10/1975 | Miller . | |
| 3,986,505 | 10/1976 | Power | 128/849 |
| 4,033,341 | 7/1977 | Scrivens | 128/852 |
| 4,275,719 | 6/1981 | Mayer . | |
| 4,323,062 | 4/1982 | Canty | 128/852 |
| 4,334,529 | 6/1982 | Wirth | 128/852 |
| 4,367,728 | 1/1983 | Mutke . | |
| 4,476,860 | 10/1984 | Singer . | |
| 4,664,103 | 5/1987 | Martin . | |
| 4,739,753 | 4/1988 | Brehm | 128/849 |
| 4,966,168 | 10/1990 | Glassman | 128/854 |
| 5,010,899 | 4/1991 | Thomson | 128/853 |
| 5,222,507 | 6/1993 | Taylor | 128/853 |
| 5,226,815 | 7/1993 | Bowman | 128/853 |

*Primary Examiner*—Robert A. Hafer
*Assistant Examiner*—Michael O'Neill
*Attorney, Agent, or Firm*—Frost & Jacobs

[57] ABSTRACT

A surgical drape has a series of retractor tunnels on opposite lateral sides of a fenestration for accommodating a vertically extending rail clamp of a table mounted retractor system. The retractor tunnels are defined by first and second portions of the sides. The first and second sides are secured to each other at longitudinally spaced intervals. The drape has flaps that are selectively movable to a position covering the retractor tunnels whenever they are not in use.

10 Claims, 3 Drawing Sheets

SURGICAL DRAPE WITH RETRACTOR TUNNELS

TECHNICAL FIELD

The invention relates generally to surgical drapes of the type used to cover a patient lying on an operating table during a surgical procedure, and more particularly concerns a surgical drape adapted to accommodate a table mounted retractor system, and to permit the retractor system to extend above the operating table without compromising the sterility of the area above the operating table surface.

BACKGROUND OF THE INVENTION

It is common practice to cover patients with surgical drapes as they are undergoing surgical procedures on an operating table. Such drapes typically cover the patients as they are lying on the operating table in a reclined position, with the operating table elevating the patients to an approximately waist high level above the floor. The drape generally has a central portion covering both the patient and the top surface of the operating table, and lateral side portions that extend downwardly toward the floor on opposite sides of the central portion to cover the sides of the operating table.

Among other functions, surgical drapes are intended to provide a contamination barrier, and to maintain a sterile environment in the surgical operating zone above the drape. In the past, this goal of maintaining the sterility of this operating zone sometimes has been compromised by the use of table mounted retractor systems. Table mounted retractor systems typically include a vertically extending rail clamp that is attached to the side of the operating table. This rail clamp extends upwardly to a position above the patient where it supports the end of a horizontally extending cross bar. The cross bar extends above the patient's area of surgical interest and, in turn, adjustably supports a retractor.

When, as is desirable, the surgical drape extends downwardly over the side of the operating table, the rail clamp of a table mounted retractor system can be mounted either on top of or below the surgical drape. Either of these options has presented problems in the prior art. The clamps that are used to attach the rail clamp to the operating table over the drape produce a shearing force that cuts the drape material. On the other hand, attaching the rail clamp to the operating table under the drape, and pulling the drape up around the rail clamp, potentially brings contamination in the surgical field above the operating table surface. The only other option, cutting a hole in the drape, only is available for disposable drapes. Furthermore, even when holes are cut in the drape material for accommodating the retractor rail clamp, it commonly occurs that the hole is cut too largely, exposing the non-sterile area beneath the drape.

SUMMARY OF THE INVENTION

Accordingly, it is a primary object of the invention to provide a surgical drape that accommodates a table mounted retractor without compromising the sterile environment of the operating zone above the drape.

It is another object of the invention to provide a reusable surgical drape that easily can be used either with or without a table mounted retractor system.

Another object of the invention is to provide a surgical drape that effectively operates as a contamination barrier after removal of a table mounted retractor system.

Additional objects, advantages, and other novel features of the invention will be set forth in part in the description that follows and in part will become apparent to those skilled in the art upon examination of the following or may be learned with the practice of the invention. The objects and advantages of the invention may be realized and attained by means of the instrumentalities and combinations particularly pointed out in the appended claims.

To achieve the foregoing and other objects, and in accordance with the purposes of the present invention disclosed herein, an improved surgical drape for use with a table mounted retractor system is provided. The drape includes a sheet of material having a longitudinal axis extending in a first predetermined direction with a central section adapted for covering a patient lying on a surgical table elevated above the floor. The central portion includes a fenestration for permitting surgical access to a patient positioned beneath the sheet, and lateral side sections extending outwardly from the central section and downwardly toward the floor on opposite lateral sides of the longitudinal axis for covering the sides of the surgical table. An elongated opening is provided in at least one of the side sections. The elongated opening is located proximal to the central section and functions to form a tunnel for accommodating a retractor attached to a side rail of the surgical table. This retractor tunnel allows the retractor to extend through the sheet of material. The elongated opening extends in a direction generally parallel to the longitudinal axis of the drape and is defined by separatable portions of the side section in overlying relationship to the other. A flap is hingeably positioned adjacent to the elongated opening and is secured to the side section intermediate of the elongated opening and the central section. The flap is movable between first position and second positions and is positioned so as to cover the elongated opening in its first position and to uncover the elongated opening in its second position. The elongated openings preferably are provided in each of the two lateral side sections to add flexibility.

In accordance with another specific aspect of the invention, the separatable portions of the side section forming the elongated opening are secured to each other at longitudinally spaced intervals of the opening, thereby dividing the elongated opening into a series of pockets and reducing gravitationally induced separation of the separatable portions.

According to another aspect of the invention, the flap is hingeably secured to the sheet material between the elongated opening and the fenestration in the central section along a line that extends longitudinally and is located laterally inwardly of the elongated opening. The flap is preferably secured in the second position when the drape is used with a table mounted retractor system.

In another aspect of the invention, the elongated opening includes a visually distinctive binding secured to the edge of at least one of the separatable portions defining the elongated opening.

BRIEF DESCRIPTION OF THE DRAWINGS

The accompanying drawings, incorporated in and forming a part of the specification, illustrate several aspects of the present invention, and together with the

Figure 1:
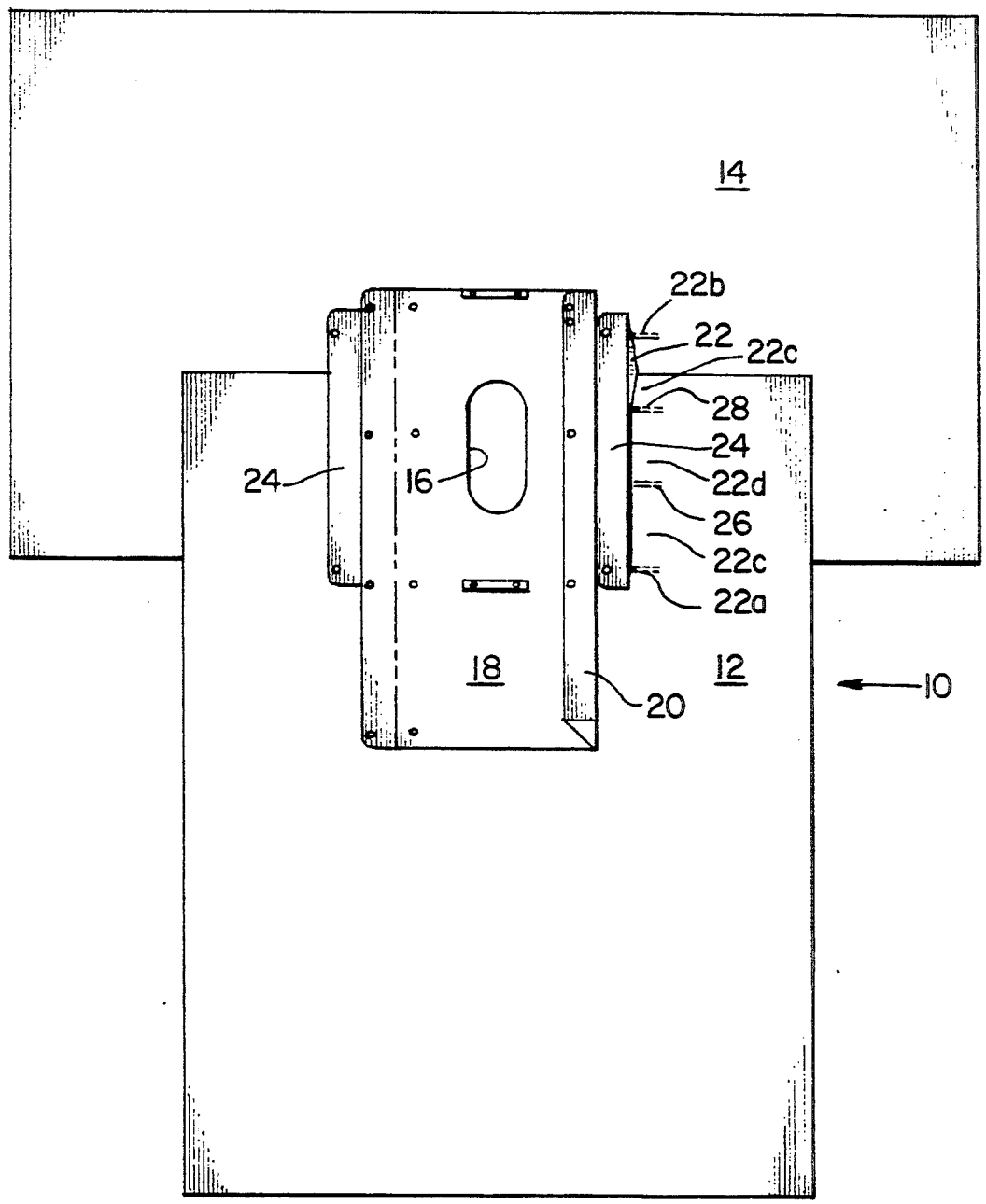
Figure 2:
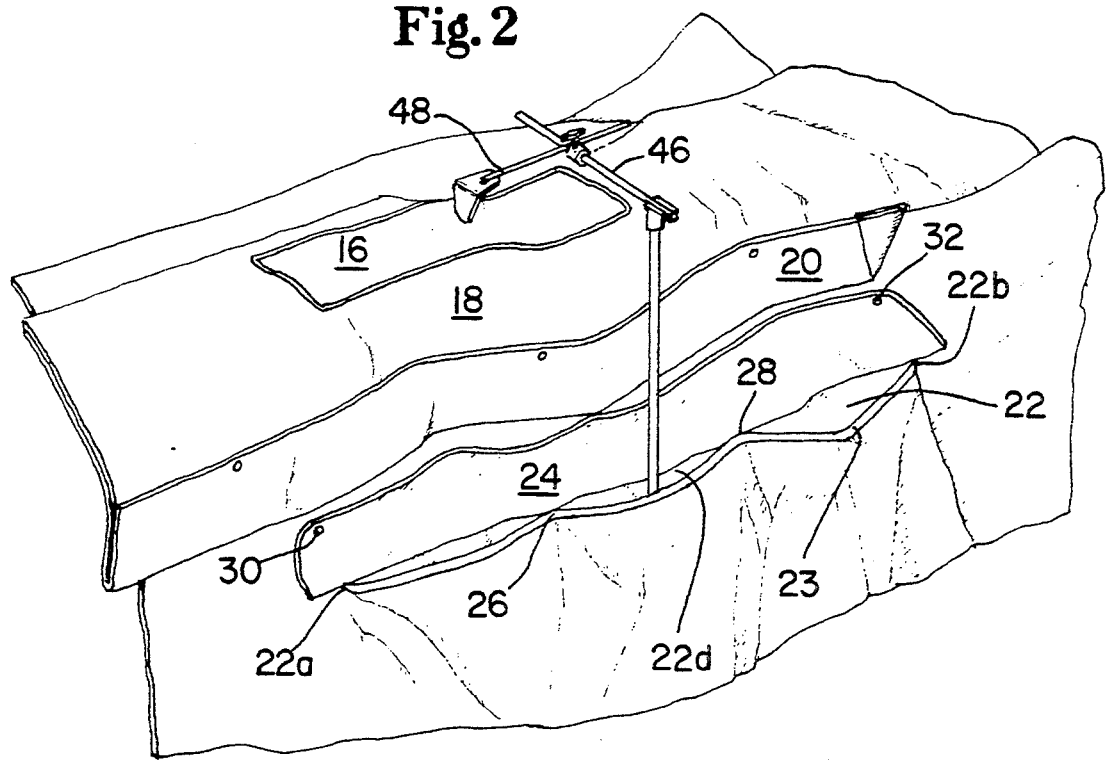
Figure 3:
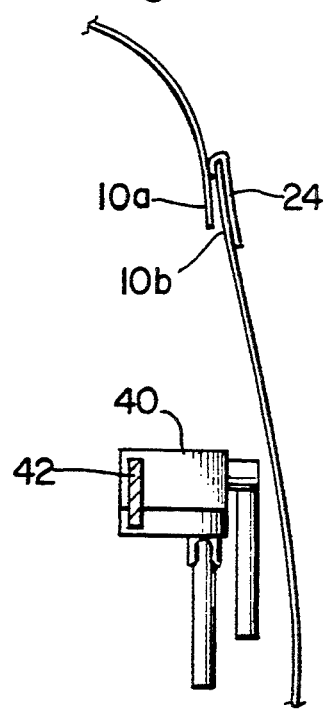

3 description, serve to explain the principles of the invention. In the drawings:

FIG. 1 is a top plan view of a surgical drape constructed in accordance with the principles of the present invention;

FIG. 2 is a perspective view of an operating table covered by the surgical drape of FIG. 1 with a table mounted retractor system extending through retractor tunnels on the side of the drape;

FIG. 3 is a side elevational view of the surgical drape of FIG. 2 showing the drape in its relationship with an underlying operating table with a flap in a closed position covering the retractor tunnels.

Figure 4:
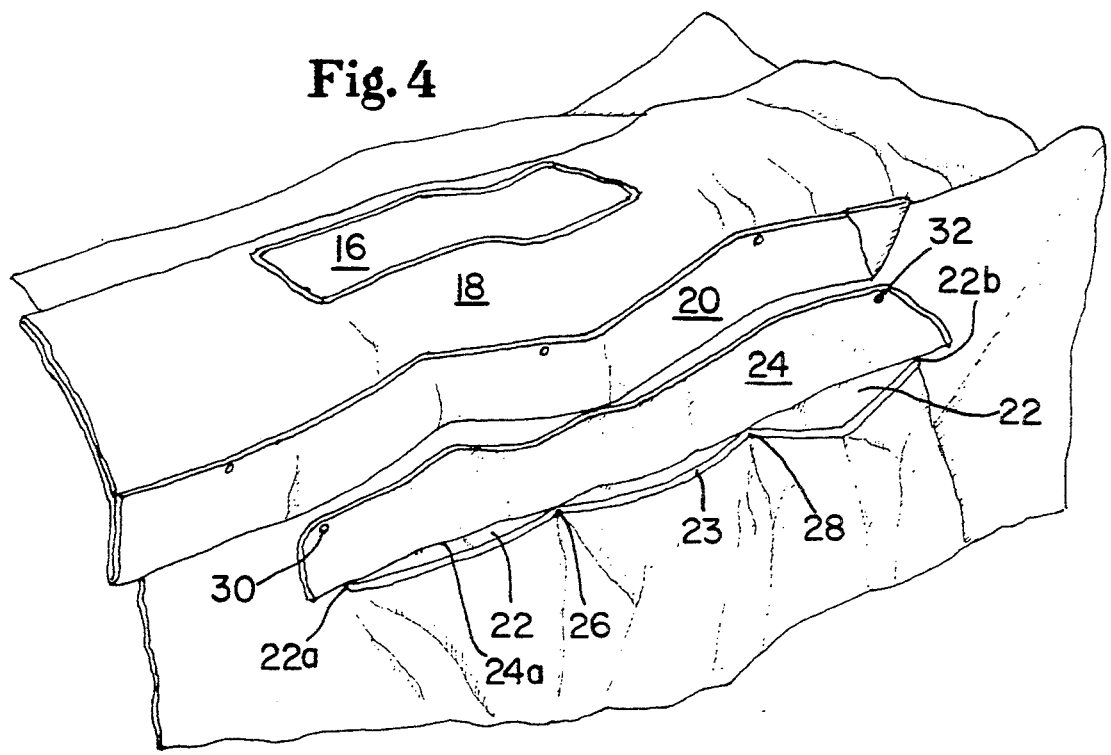
Figure 5:
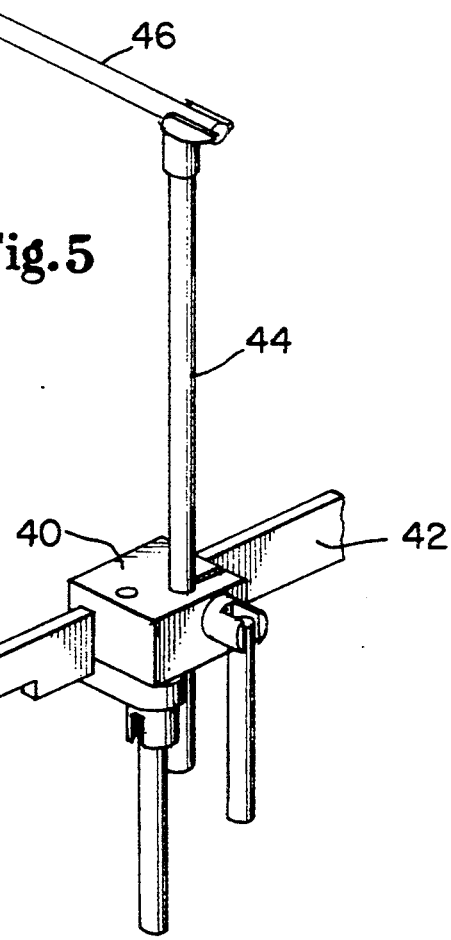
Figure 6:
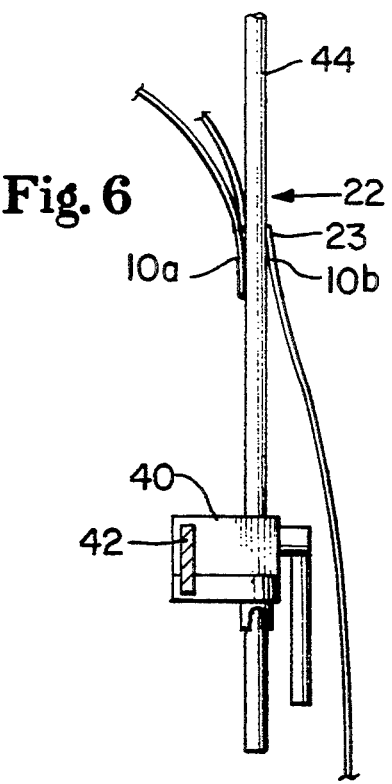

FIG. 4 is a perspective view similar to FIG. 2, but with the table mounted retractor system removed;

FIG. 5 is a perspective view of the table mounted retractor system of FIG. 2 as it is mounted to the operating table frame; and FIG. 6 is a side elevational view similar to that of FIG. 3, but showing the retractor system extending through one of the retractor tunnels.

Reference will now be made in detail to the present preferred embodiment of the invention, an example of which is illustrated in the accompanying drawings.

DETAILED DESCRIPTION OF THE INVENTION

Referring now to the drawings, FIG. 1 shows one preferred embodiment of the invention in which a sheet of fabric material, generally indicated by the drawing numeral 10 is shown. The sheet 10, specifically illustrated in the drawings as a winged laparotomy drape, is actually formed of two segments 12 and 14 that are seamed together to jointly form a T-shaped configuration. However, as will be apparent from the following to those skilled in the art, neither the precise configuration of the sheet 10 nor the number of segments that are secured together to form the sheet is critical to the present invention, and the invention described herein can be used in connection with surgical drapes of virtually any configuration. Consequently, for purposes of the present specification and claims, the term "sheet" will be used to include both sheets that are formed from a single piece of material, and sheets that are seamed or otherwise secured together to form a single functional unit.

The illustrated sheet 10, which is intended to cover a patient, and the top and side surfaces of an operating table, includes a centrally disposed and longitudinally oriented fenestration 16 for accessing a surgical area of the patient beneath the sheet 10. The fenestration 16, which is specifically illustrated as having a longitudinally extending oval configuration, is surrounded by a trough system, generally indicated by the drawing numeral 18. As will be immediately apparent to those skilled in the art, the trough system functions to control the flow of those fluids emanating from and those fluids used with the surgical area. The trough system, which is conventional and well known in the art, includes an absorbent material 18 with a fluid resistant backing 20 which are secured to the top of the sheet 10. In the drawing of FIG. 1, the backing 20 is seen only on the longitudinal edges of the trough system where the edges of the trough system are folded over to inhibit lateral flow of fluids from the trough area. Inasmuch as trough systems of the type illustrated are well-known in the art and form no part of the present invention per se, further description thereof will be omitted for purposes of brevity.

Turning now to FIGS. 2 and 4, it can be seen that the sheet 10 is designed to cover the top and side portions of an operating table, which operating table conventionally supports a surgical patient in a reclined position on an elevated top horizonal surface above the operating room floor. In such use, the central section of the illustrated drape 10 (which includes portions of both segments 12 and 14) covers both the patient and the top surface of the operating table with outwardly and downwardly extending lateral side sections (which, again, includes portions of both segments 12 and 14) covering the lateral sides of the operating table. The drape 10 also may include top and bottom side sections for covering the top and bottom sides of the operating table. Thus, unless otherwise indicated from the context of usage, the term "side section" will be used in this specification and claims to include lateral, top and bottom sides.

In accordance with the teaching of the invention, each of the lateral side sections of the illustrated sheet 10 includes an elongated opening 22. Each of these elongated openings 22 is laterally positioned with respect to the fenestration 16 and extends in a direction generally parallel to the longitudinal axis of the drape. As perhaps best appreciated from jointly viewing FIGS. 2, 3 and 6, these elongated openings 22 are defined by separatable portions 10a and 10b of the side section that are positioned in overlying relationship to each other when the elongated openings are not in use, as specifically illustrated in FIG. 3. In the illustrated embodiment, these separatable portions 10a and 10b extend between seams 22a and 22b. Visually distinctive bindings 23 preferably are secured to the edges of the separable portion 10b to alert surgical personnel of the discontinuity in the contamination barrier provided by the sheet 10. Flaps 24 are provided to overfold and cover the elongated openings 22 when they are not in use. The flaps 24 are hingeably secured to the sheet 10 at a location adjacent to each of the elongated openings 22. The flaps are secured to the sheet 10 along hinge lines 24a that are parallel to the elongated openings 22 and are located intermediate the respective elongated openings 22 and the fenestration 16. These flaps 24 are movable from a first position, illustrated in FIG. 3 (and on the left side of FIG. 1) in which the flaps overlap and cover the elongated openings 22, to a second position, illustrated in FIGS. 2, 4 and 6, in which the elongated openings 22 are uncovered. The flaps 24 are releasably secured in the second, open position through the agency of a releasable fastening system. The specific fastening system used for this purpose in the illustrated embodiment includes male snaps 30 and 32 located proximal to the longitudinal ends of the flaps 24, with complementary female snaps located between the flap hinge lines 24a and the trough system. Preferably, the female snaps are secured on the sheet 10 by twill tape, as is well known in the art, so as not to penetrate the sheet 10 and form a potential electrical path with the patient. Other types of fastening systems can be used, however, without departing from the spirit of the invention.

To allow maximum flexibility, the elongated openings 22 extend for a substantial longitudinal distance along the respective side portions of the sheet 10. For example, in the specific embodiment illustrated, the sheet 10 (including both the segments 12 and 14) extends for approximately 130 inches in the longitudinal direction and the elongated openings extending for approximately 26 to 30 inches. The flaps 24 extend somewhat beyond each of the longitudinal ends of the elongated openings 22, preferably for an inch or more, so as to insure total coverage of the elongated openings 22 when the flaps 24 are in the second, closed position. In order to maximize flexibility, the optimal length of the elongated openings 22, however, is such that gravity induced drooping of the outermost of the separatable portions may occur with respect to the innermost portions. To minimize this tendency, the inner and outer portions of the side section forming the elongated openings, portions 10a and 10b respectively, are secured to each other at longitudinally spaced intervals along the elongated opening 22, as shown at locations 26 and 28 in the drawings. Securing the separatable portions 10a and 10b at spaced intervals also divides the elongated openings 22 into a series of individual retractor tunnels, three such retractor tunnels 22c, 22d, and 22e, being depicted in the illustrated embodiment.

As indicated above and depicted in FIGS. 2 and 6, the elongated openings 22 function as tunnels for accommodating a retractor attached to the side rail of the operating table. FIGS. 2, 3, 5 and 6 show one table mounted retractor system that may be used advantageously with drapes constructed in accordance with the principles of the invention. Referring specifically to FIG. 5, a rail clamp 40 of the retractor system is shown attached to the side rail frame 42 of an operating table. The rail clamp 40 supports a vertical rail bar 44 which, as shown in FIGS. 2 and 6, extends through the retractor tunnel 22d. A horizontally extending cross bar 46 (shown in FIGS. 2 and 5) is secured to the top of the rail bar 44. The horizonal cross bar extends outwardly over the top surface of the operating table where it, in turn, supports a retractor 48 in the area over the fenestration 16, as illustrated in FIG. 2.

The drape of the present invention may be used most advantageously when there is a need to use a table mounted retractor system. When this need arises, the flaps 24 are moved to their second position, and, to maximize the principles of accepted aseptic teachings, the drape preferably would be presented to the surgical team in the mode illustrated in FIGS. 2, 4, and 6, with the flap 24 adjacent the selected retractor mounting area secured in the second position by the snaps 30 and 32. While the flap 24 is in this second position, the vertical rail bar 44 of the table mounted retractor system is passed through one of the retractor tunnels formed by the elongated opening 22, as illustrated in FIG. 6. When the surgical procedure has advanced to the point where the table mounted retractor is no longer needed, and the table mounted retractor system is removed, the flap 24 of the illustrated embodiment would be moved to its first position, which is illustrated in FIG. 3. When moved to this first position, a sterile side of the flap 24 then is positioned to overlie the outer portion 10b of the separable portions forming the elongated openings 22, with the portions 10a and 10b also being in overlying, contacting relationship.

It also will be appreciated that the drape of the present invention has the flexibility for use without a table mounted retractor system. Whenever such use is contemplated, the drape preferably is presented to the surgical team with the flap 24 in the first position, as illustrated in FIG. 3. With the flap secured in this position, the drape 10 provides an effective contamination barrier over the elongated openings 22, and the drape 10 is used in the same manner as conventional surgical drapes.

In summary, numerous benefits have been described which result from employing the concepts of the invention. The invention can be used advantageously either with or without a table mounted retractor system, and when used with such a system, allows the use of a table mounted retractor system without compromising either the sterility or the long term integrity of the drape. The visually distinctive binding on the edges of the elongated opening alert surgical personnel of the boundaries of the opening. Quite advantageously, the invention allows the use of a table mounted retractor system without securing the mounting clamp of the retractor system to the operating table side rail over the drape, thereby avoiding the damage that frequently results from such mounting. The invention also avoids incurring the contamination that results from pulling the drape up around the rail.

The foregoing description of a preferred embodiment of the invention has been presented for purposes of illustration and description. It is not intended to be exhaustive or to limit the invention to the precise form disclosed. Obvious modifications or variations are possible in light of the above teachings. For example, the invention can use virtually any configuration of drape and can be used with drapes of various fabrics. Various fastening systems for securing the flap in its open position also may be used. The embodiment was chosen and described in order to best illustrate the principles of the invention and its practical application to thereby enable one of ordinary skill in the art to best utilize the invention in various embodiments and with various modifications as are suited to the particular use contemplated. It is intended that the scope of the invention be defined by the claims appended hereto.

I claim:

1. A surgical drape adapted for covering a patient on an elevated surgical table of the type having a side rail and an upstanding retractor mounted on said rail, said drape comprising:

a) a sheet of material, said sheet having a first axis extending in a first predetermined direction with a central section adapted for covering a patient lying on a surgical table elevated above a floor, said central portion including a fenestration for permitting surgical access to a patient positioned beneath the sheet, said sheet further having at least one side section extending outwardly from the central section on at least one side of the first axis for covering at least one side of the surgical table, said at least one side section being adapted to extend downwardly toward the floor;

b) an elongated opening in said at least one side section, said elongated opening being located proximal to the central section, said elongated opening forming a tunnel for accommodating a retractor attached to a side rail of the surgical table and extending through the sheet of material, said elongated opening extending in a direction generally parallel to the first axis of the drape and being defined by first and second portions of said at least one side section, one of said first and second portions being in overlying relationship to the other; and c) a flap positioned adjacent to said elongated opening and secured at a location intermediate of the elongated opening and the central section, said flap being movable between first and second positions and positioned so as to cover the elongated opening in said first position and not to cover at least a portion of said elongated opening in said second position.

2. A surgical drape as recited in claim 1 wherein said first and second portions of the side section forming said elongated opening are secured to each other at longitudinally spaced intervals of the opening, thereby dividing the elongated opening into a series of retractor tunnels and reducing gravitationally induced separation of the separatable portions.

3. A surgical drape as recited in claim 1 wherein elongated openings are provided in each of said lateral side sections on opposite sides of the fenestration in the central section.

4. A surgical drape as recited in claim 1 wherein said flap is secured to said sheet material along a line extending in a direction generally parallel to the longitudinal axis of the sheet, and is located laterally inwardly of the elongated opening, between the elongated opening and the fenestration in the central section.

5. A surgical drape as recited in claim 1 further including means for securing the flap in said second position.

6. A surgical drape as recited in claim 1 further including a visually distinctive binding secured to the edge of at least one of said first and second portions defining the elongated opening.

7. A surgical drape as recited in claim 1 wherein the sheet is formed of a fabric material.

8. A surgical drape as recited in claim 1 wherein the first axis extends in a direction generally parallel to the longitudal axis of the sheet.

9. A surgical drape as recited in claim 3 wherein said first and second portions of the side sections forming said each of the elongated openings each are secured to each other on its respective side at longitudinally spaced intervals of the opening, thereby dividing the elongated opening into a series of retractor tunnels and reducing gravitationally induced separation of the separatable portions.

10. A surgical drape adapted for covering a patient on an elevated surgical table of the type having a side rail and an upstanding retractor mounted on said rail, said drape comprising:

a) a sheet of fabric material, said sheet having a longitudinal axis extending in a first predetermined direction with a central section adapted for covering a patient lying on a surgical table elevated above a floor, said central portion including a fenestration for permitting surgical access to a patient positioned beneath the sheet, said sheet further having side sections on opposite lateral sides of the central section, said side sections extending laterally outwardly from the central section on opposite sides of the longitudinal axis for covering the lateral sides of the surgical table, each of said side sections being adapted to extend downwardly toward the floor;

b) an elongated opening in each of said side sections, said elongated openings being located on opposite side sections proximal to the central section, each of said elongated openings forming a tunnel for accommodating a retractor attached to a side rail of the surgical table and extending through the sheet of material, each of said elongated openings extending in a direction generally parallel to the longitudinal axis of the drape and being defined by first and second portions of the respective side sections, said first and second portions on each side being in overlying relationship to the other, said first and second portions of each of said elongated openings being secured to each other to each other at longitudinally spaced intervals; and c) a flap positioned adjacent to each of said elongated openings, each of said flaps being secured at a location intermediate of the elongated opening to which it is adjacent and the central section, each of said flaps being movable between first and second positions and positioned so as to cover the elongated openings to which it is adjacent in said first position and not to cover at least a portion said elongated opening to which it is adjacent in said second position.

* * * * *